(12) United States Patent
Ranjan et al.

(10) Patent No.: US 7,059,174 B2
(45) Date of Patent: Jun. 13, 2006

(54) METHOD AND PROBE FOR MEASURING HYDRAULIC CONDUCTIVITY OF SOIL

(75) Inventors: Ramanathan Sri Ranjan, Industry Liaison Office, 631 Drake Centre, Winnipeg, Manitoba (CA) R3T 5V4; Martin Petrak, 43 Braswell Bay, Winnipeg, Manitoba (CA) R3X 2B6

(73) Assignees: Ramanathan Sri Ranjan, Winnipeg (CA); Martin Petrak, Winnipeg (CA)

( * ) Notice: Subject to any disclaimer, the term of this patent is extended or adjusted under 35 U.S.C. 154(b) by 0 days.

(21) Appl. No.: 10/513,888

(22) PCT Filed: May 9, 2003

(86) PCT No.: PCT/CA03/00655

§ 371 (c)(1),
(2), (4) Date: Nov. 9, 2004

(87) PCT Pub. No.: WO03/095985

PCT Pub. Date: Nov. 20, 2003

(65) Prior Publication Data

US 2005/0177309 A1    Aug. 11, 2005

Related U.S. Application Data

(60) Provisional application No. 60/379,588, filed on May 13, 2002.

(51) Int. Cl.
*G01N 15/08* (2006.01)
(52) U.S. Cl. ............................................... 73/38
(58) Field of Classification Search .................... 73/38; 405/129.5
See application file for complete search history.

(56) References Cited

U.S. PATENT DOCUMENTS

| 2,345,935 | A |   | 4/1944 | Hassler |           |
|-----------|---|---|--------|---------|-----------|
| 4,150,578 | A | * | 4/1979 | Swartz  | ... 73/725 |
| 6,061,634 | A | * | 5/2000 | Belani et al. | ... 702/12 |
| 6,098,448 | A | * | 8/2000 | Lowry et al. | ... 73/38 |
| 6,236,941 | B1| * | 5/2001 | Kram et al. | ... 702/12 |

FOREIGN PATENT DOCUMENTS

| DE | 197 25 035 | 10/1998 |
| FR | 2605740    | 4/1988  |
| WO | 01 59248   | 8/2001  |

\* cited by examiner

*Primary Examiner*—Hezron Williams
*Assistant Examiner*—Paul M. West
(74) *Attorney, Agent, or Firm*—Ryan W. Dupuis; Michael R. Williams; Adrian D. Battison

(57) ABSTRACT

Agricultural waste lagoons are the predominant method currently utilized to contain large quantities of livestock by-products such as manure. Clay liners are the most common materials used to line the bottom of storage lagoons in order to prevent waste effluent seepage. Clay liners are an economical lining material and have a hydraulic conductivity of less than $1 \times 10^{-7}$ cm/s. Proper containment of waste in storage lagoons is critical to avoid the implications of local groundwater contamination. A hydraulic conductivity probe was designed to alleviate the negative aspects of the current methods used to determine hydraulic conductivity. The probe includes a housing for insertion into the ground, electrical potential gradient means for generating an electrical potential gradient in the ground and pressure sensing means for measuring changes in pressure in the ground.

28 Claims, 3 Drawing Sheets

METHOD AND PROBE FOR MEASURING HYDRAULIC CONDUCTIVITY OF SOIL

This application is a 371 national phase application of PCT/CA03/00655 and claims the benefit under 35 U.S.C. Section 119(e) of U.S. provisional application 60/379,588 filed May 13, 2002.

FIELD OF THE INVENTION

The present invention relates to a probe for measuring hydraulic conductivity of soil, and more particular to a method of use of the probe in situ.

BACKGROUND

Groundwater contamination is a growing concern in the agricultural and waste management industry. Seepage losses from animal-waste storages, municipal lagoons, and industrial waste retention ponds including mine tailings retention ponds, are common sources of groundwater pollution. A livestock operation produces large amounts of organic effluent and often is stored on site. Typically, the most feasible and cost effective method to store and or treat organic waste is to contain the waste in a lagoon or retention pond. The bottom of these lagoons is generally made from a semi-impermeable layer comprised of synthetic or clayey soil material. In most cases, the cost of synthetic impermeable liners is more expensive than compacted clay liners and therefore the clay liners are used more often for agricultural waste management applications.

The main concern relating to clay liners is their ability to properly maintain a relatively impermeable barrier between the waste and the surrounding material over a length of time without seepage losses that could impact the groundwater quality in the area. When manure storage lagoons require maintenance or are emptied for organic fertilizing purposes, they are usually agitated to mix the solids that have settled out over a period of time. This agitation process can loosen and partially remove the upper layer of the saturated clay liner, which inevitably causes the deterioration in the liner thickness and a less desirable hydraulic conductivity. The guidelines given by the United States Environmental Protection Agency (EPA) for the thickness of a clay liner is one metre and the hydraulic conductivity (K), cannot be greater than $1 \times 10^{-7}$ cm/s.

Estimation of soil hydraulic conductivity at a particular site is challenging and expensive at times in order to produce acceptable results. Measuring the permeability of a saturated clay matrix is important in the design of lagoon liners. The ability to predict the rate of nitrate contaminant transport is vital information for evaluating future lagoon sites. Accurate estimates of the hydraulic conductivity act as a tool for monitoring existing sites.

There are a number of methods that are in use to measure the saturated hydraulic conductivity of soils, but these are typically overly expensive, complicated, time consuming and/or produce false results. A sample can be obtained as a core from the lagoon bottom, after pump out, and laboratory tests can estimate the hydraulic conductivity (K), however this disturbed specimen may not be a true representation of the in situ conditions. Pumping the storage dry would cause shrinkage cracks, which could create macropores and fissures, which will act as preferential flow paths for contaminants. To protect the integrity of the clay liner, manure storages are never completely emptied during pump out and this makes it extremely difficult to obtain core samples from the bottom covered with liquid manure slurry. Getting technicians to retrieve core samples under such conditions will be a difficult and time consuming task. Since the manure storages are never emptied completely it is impossible to locate problems by visual inspection by regulators. Currently, core samples are obtained using drill rigs located on the frozen ice layer above the stored manure. However, this is limited to a small window of time during which the outside temperatures remain below sub-zero temperatures (<−15 degrees Celsius) so that the ice cover remains thick enough to support a drill-rig.

Another method commonly used to determine K is a standard borehole pump test, but this intrusive method disturbs the thin upper organic sludge-clay interface and exposes that portion of liner to an aerobic environment. Chemical reactions and biological interaction with the aerobic environment changes the in situ characteristics of the liner. Also, the borehole pump test is more applicable to highly permeable aquifers. However, because of the low hydraulic conductivity of compacted clay, the conventional borehole tests cannot be used efficiently for the lagoons. It is essential to develop an accurate monitoring tool to determine a clay liners performance over time in order to minimize seepage below retention ponds and lagoons to ensure the safety of rural groundwater aquifers.

As noted above, hydraulic conductivity of soils is determined by a number of techniques, but in practice, there are only three main methods: laboratory tests, field tests and empirical methodologies (Domenico and Schwartz 1997 pg.44). The theory of hydraulic conductivity, Darcy's Law and Horslev's Method is reviewed in detail. An overview of electro-kinetics and how it relates to hydraulic conductivity is provided.

Most methods used to measure hydraulic conductivity are derived from the fluid motion through porous media law known as Darcy's Law. This law was named after a French civil engineer Henry Darcy whose experimental methodology for measuring the rate of flow through a porous medium was published in 1856. Darcy's experiment includes a cylinder of length (L) containing a porous medium with manometers attached at either end to measure the water pressure head as water passes through the column. From this simple experiment, Darcy found that discharge Q, is proportional to the change in head pressure and inversely proportional to the length of the column containing the porous media (Fetter 1994). From these relationships Darcy formulated the Hydraulic conductivity constant K, which estimates the rate of flow through a porous medium per unit hydraulic gradient per unit cross-sectional area. Discharge is expressed in the general form $Q=-KA(dh/dl)$, where Q is the discharge ($L^3/T$) and A is the cross sectional area through which the fluid passes and has units $L^2$. The term (dh/dl) is referred as the hydraulic gradient, which is a ratio of the difference in head ($h_1-h_2$) between two points and the length separating them ($\Delta L$). The proportionality coefficient K represents the hydraulic conductivity, which has the same units as velocity L/T. The negative sign represents the movement of a fluid in the direction of decreasing hydraulic head (Fetter 1994). The hydraulic conductivity is dependent on fluid properties such as density and kinematic viscosity as well as properties of the porous medium.

Domenico and Schwartz (1997) express the hydraulic conductivity K, in terms of properties that characterize the fluid (water in this case) and porous medium (sand in this case). This relationship is expressed as $$K = \frac{Nd^2 \rho_w g}{\mu} = \frac{k_i \rho_w g}{\mu}$$

Where

N=Dimensionless shape factor of the sand particle
$\rho_w$=Density of water at a specific temperature (M/L$^3$)
g=Acceleration due to gravity (L/T$^2$)
d=Mean grain diameter (L)
$\mu$=Dynamic viscosity of fluid (M/TL)
$k_i$=Intrinsic permeability of the porous medium.(L$^2$)

The intrinsic permeability $k_i$ is a property of the porous medium that is equal to Nd$^2$ in the given relationship. The intrinsic permeability is independent of the fluid properties and therefore is a direct measure of flow resistance through a medium. Given a particular fluid, the higher the permeability of a porous homogeneous medium, the greater the ability to transmit flow.

The hydraulic conductivity can be determined in the laboratory using several different techniques, but these methods lack the characteristics of in situ methods that minimally disturb the soils. Two of the most common methods of determining hydraulic conductivity in the laboratory are Constant Head and Falling Head methods.

The constant head permeameter method delivers a constant supply of fluid to a porous medium to maintain a given pressure head. The hydraulic $$K = \frac{LQ}{H\pi R^2}$$

conductivity is specified by the relationship:

where Q is the volume flow rate defined by the cross sectional area of the tube multiplied by the velocity of the fluid. The constant head permeameter is most suitable for estimating the hydraulic conductivity of coarse sands and gravels because of the high permeability of these materials, while the falling head permeameter is more appropriate for fine silt and clay like soils (Wanielista, Kersten and Eaglin 1997).

The falling head permeameter uses a similar relationship for the discharge Q. The falling rate of the water level in the stand pipe is expressed by:

$$Q = Av = \pi r^2 \left(\frac{dh}{dl}\right)$$

Where,
v=falling head velocity.
And Darcy's Law can be applied to the soil column as:

$$Q = \pi R^2 K \left(\frac{H}{L}\right)$$

After equating both of these equations and integrating, the hydraulic conductivity for a falling head permeameter is represented by the following relationship:

$$K = \frac{\pi r^2 L}{\pi R^2 t} \ln\left(\frac{H_1}{H_2}\right)$$

where $H_1/H_2$ is the head ratio of initial to final head at a time t(s).

A flexible wall permeameter is a test chamber that contains a porous medium, which is used for both the constant and falling head methods. There are strict guidelines for laboratory procedures when acquiring and testing a porous material sample and are outlined by the American Society for Testing and Materials (ASTM D 5084–90). The laboratory techniques discussed are standard methods of determining K from small soil samples taken from the field.

Field techniques are more accurate methods for estimating in situ hydraulic conductivity. Small-scale lab tests are not representative of the non-uniformities, which are found in geological deposits under subsurface conditions. Examples of such naturally occurring non-uniformities are macro pores, fissures and small channels including worm and rodent holes. These soil structure abnormalities are very challenging to duplicate in an experimental setting and the results from which therefore are only estimators of in situ hydraulic conductivity.

Daniel (1989) explains that in situ permeameters can be divided into four categories. The first two categories are borehole and porous probe permeameters that are used to measure low permeability soils and the other two are infiltrometers and lysimeters that estimate K for permeable agricultural type soils.

The borehole or augerhole method is one of the most popular site investigative and monitoring practices of estimating hydraulic conductivities for relatively shallow water tables. One of these techniques is called the Hvorslev Method or Slug test method, which drills out a standard borehole and inserts a piezometer. In one variation, the piezometer may be installed into sand and therefore does not require a sand pack around well screen to minimize entry losses.

When the static water level (H) is measured, a unit volume of water or metal slug is either introduced or removed out from the well. If a slug is suddenly introduced, then the water level will rise to the initial falling head Ho. As the head decreases, the time is recorded until the water level returns close to the static level H. Water levels can be measured accurately inside the piezometers with pressure transducers that measure the change in head pressure. The data is then plotted where the natural logarithm of the ratio of H/Ho produces a relatively straight line with respect to time. Hvorslev (1951) developed the relationship between the measured hydrostatic head and the pore pressures in the adjacent soil formation as water flowed into the piezometer. Hvorslev noticed a lag time required to equilibrate the pressure difference assuming that a constant flow is maintained at the initial rate into the piezometer and found that the time lag was inversely proportional to the hydraulic conductivity of the adjacent soil. The following equation relates time lag and K:

$$T_o = \frac{A}{FK}$$

where, $T_o$=basic lag time for the head level to fall to 37 percent of the initial water level;

F=shape factor which varies with borehole geometry; and

A=Cross sectional area of the piezometer.

When the time lag is established and the shape factor is identified for a particular piezometer or instrument, the above relationship can be rearranged to solve for the hydraulic conductivity of the adjacent soil.

The borehole in situ methods have several limitations such as high implementation costs, poor estimators of the vertical component of hydraulic conductivity and the role of specific storage $S_s$ is completely ignored (Demir, Z. and Narasimhan, T. N. 1994). The specific storage is the amount of water released or absorbed into storage per unit of volume of a porous medium per unit change in fluid head (Fetter, 1994).

A similar borehole method uses the Boutwell Permeameter, which measures both horizontal ($K_h$) and vertical ($K_v$) coefficients of permeability. This is an improvement from the previous method, but both methods measure a relatively small volume of soil (<<1 m³) and can take any where from a few days to weeks for silty-clay soils with K<1×10⁻⁷ cm/s (Daniel, 1989).

Daniel (1989) describes and summarizes nine state of the art in situ hydraulic conductivity estimation methods and instruments for compacted clay soils and lists the advantages and disadvantages of each method. The common element that plagues all in situ methods of estimating hydraulic conductivity are the errors caused by incomplete saturation of the soils (Daniel 1989).

In the laboratory there have been many efforts to relate measured values of hydraulic conductivities to various properties of porous materials (Domenico, P. A. and Schwartz, F. W. 1997).

Empirical methods are adequate for rough estimations of hydraulic conductivities, but should be used only as theoretical tools rather than for practical design applications.

Electro-osmosis is a mechanism, which induces a fluid to flow through low permeable clayey soils. When electrodes are attached to a column of saturated soil and an electrical potential gradient is applied across the soil sample, the fluid will move from the anode to the cathode. The fluid flow is induced by the electric field applied to the soil sample (Yeung, A. T., Gopinath, Sreekumar, Menon, Rajendra, M., Scott, T. B., Datla, Subbaraju. 1993). Water will move under the influence of an electrical potential gradient and the electro-osmotic flow rate can be expressed by the equation:

$$q_e = -K_e \nabla E$$

where $q_e$ is the electro-osmotic flux (m/s); and $K_e$ is the electro-osmotic conductivity (m²V×$_s$).

The electrical potential gradient is represented by $\nabla E$ and has units V/m.

Since a hydraulic gradient is induced by exposure to an electric field, a probe or device can be developed to estimate saturated hydraulic conductivity by utilizing electro-osmotic behaviour of various soils.

SUMMARY

According to one aspect of the present invention there is provided a method of measuring hydraulic conductivity in soil, said method comprising:

providing a probe having means for generating an electrical potential gradient for causing fluid flow and pressure sensing means for measuring changes in pressure;

inserting the probe into the soil;

measuring a first pressure condition within the soil using the pressure sensing means of the probe;

applying an electrical potential gradient to the soil using the electrical potential gradient means of the probe for an elapsed period of time;

measuring a second pressure condition within the soil using the pressure sensing means of the probe;

removing the application of electrical potential gradient to the soil at the end of the elapsed period of time;

measuring the pore fluid pressure as a function of time during a measured duration while the soil returns from the second pressure condition to the first pressure condition; and calculating hydraulic conductivity based upon a prescribed relationship of hydraulic conductivity and the measured duration.

The method may include calibrating the probe to determine the prescribed relationship between hydraulic conductivity and the measured duration prior to calculating the hydraulic conductivity.

The electrical potential gradient is preferably applied until a pressure condition of the soil reaches a prescribed pressure in which the prescribed pressure is an adjustable set point pressure. The electrical potential gradient is also preferably applied for a prescribed duration.

In some instances the method may include wetting the soil before measuring the first and second pressure conditions. In this instance, the probe would include a water port for introducing water into the soil which is to be sealed before measuring the first and second pressure conditions induced by the electro-osmotic method. A pressure condition of the soil should become constant after wetting the soil before measuring the first and second pressure conditions.

In further instances, the method may include bleeding air surrounding the pressure sensing means within the soil before measuring the first and second pressure conditions. In this instance, the probe preferably includes an air port for removing air from the soil surrounding the pressure sensing means. The method includes sealing the air port before measuring the first and second pressure conditions when an air port is provided.

When the probe includes two electrical potential sensors at prescribed spaced locations within the electrical gradient generated by the electrical potential gradient means, the method may include measuring electrical potential across the potential electrodes and calculating the electrical conductivity of the soil. The soil is preferably wetted before measuring the first and second pressure conditions if the calculated electrical conductivity indicates the soil is dry.

By recording the elapsed period of time of the electrical potential gradient, the electro-osmotic conductivity can be calculated based upon the elapsed period of time and a difference in magnitude between the first and second pressure conditions.

The method is particularly suited for application in situ into clay soil beneath a retention pond.

For proper sealing of the lining of a retention pond after measurement, the method preferably includes the steps of:

a) providing a probe insertion tube for slidably receiving the probe therethrough;

b) inserting the probe insertion tube into the soil prior to insertion of the probe;

c) inserting the probe into the soil by inserting the probe through the probe insertion tool;

d) removing the probe from the probe insertion tube subsequent to measurement of the first and second pressure conditions;

e) introducing soil sealing material through the probe insertion tube to fill a cavity in the soil formed by the probe; and f) removing the probe insertion tube from the soil.

A suitable soil sealing material may comprise bentonite pellets.

According to a further aspect of the present invention there is provided a probe for measuring hydraulic conductivity in soils, the probe comprising:

a housing being suitably shaped for insertion into the ground;

electrical potential gradient means for generating an electrical potential gradient in the ground surrounding the housing; and pressure sensing means for measuring changes in pressure in the porewater within the ground.

The housing preferably comprises an elongate tubular member having a pointed soil penetrating end in which the electrical potential gradient means and the pressure sensing means being located adjacent the pointed soil penetrating end.

The electrical potential gradient means may comprise first and second electrodes insulated from one another at spaced locations on the housing and an electrical power supply coupled therebetween.

When the housing extends in a longitudinal direction between an exposed end and a soil penetrating end, the first and second electrodes are preferably spaced apart from one another in the longitudinal direction of the housing.

The first electrode may be coupled to a pointed end cap at the soil penetrating end of the housing and the second electrode may be coupled to side walls of the housing when the pointed end cap is insulated with respect to the side walls of the housing.

There may be provided two electrical potential sensors supported on an insulated portion of the housing at prescribed spaced locations within the electrical gradient generated by the electrical potential gradient means.

There may be provided a plurality of apertures in the housing for communication with an internal cavity of the housing supporting the pressure sensing means therein.

There may be provided a remotely operated mechanism to cover the plurality of apertures in the housing to prevent clogging of the apertures during insertion and retrieval so as to maintain communication with an internal cavity of the housing supporting the pressure sensing means therein.

The mechanism to cover the plurality of apertures should be operable from a remote location.

The pressure sensing means preferably comprises a pressure transducer.

When the housing extends in a longitudinal direction between an exposed end and a soil penetrating end, an air port may communicate between the exposed end of the housing and the internal cavity of the housing. The air port preferably includes a valve for selectively sealing the air port in a closed position.

There may also be provided a water port communicating between the exposed end of the housing and the internal cavity of the housing, which also includes a valve for selectively sealing the water port in a closed position.

For insertion into the ground there is provided an elongate probe insertion tube for receiving the housing therein having a soil penetrating end formed of resilient material permitting the pointed end of the housing to be penetrated therethrough.

BRIEF DESCRIPTION OF THE DRAWINGS

In the accompanying drawings, which illustrate an exemplary embodiment of the present invention.

DETAILED DESCRIPTION

Figure 1:
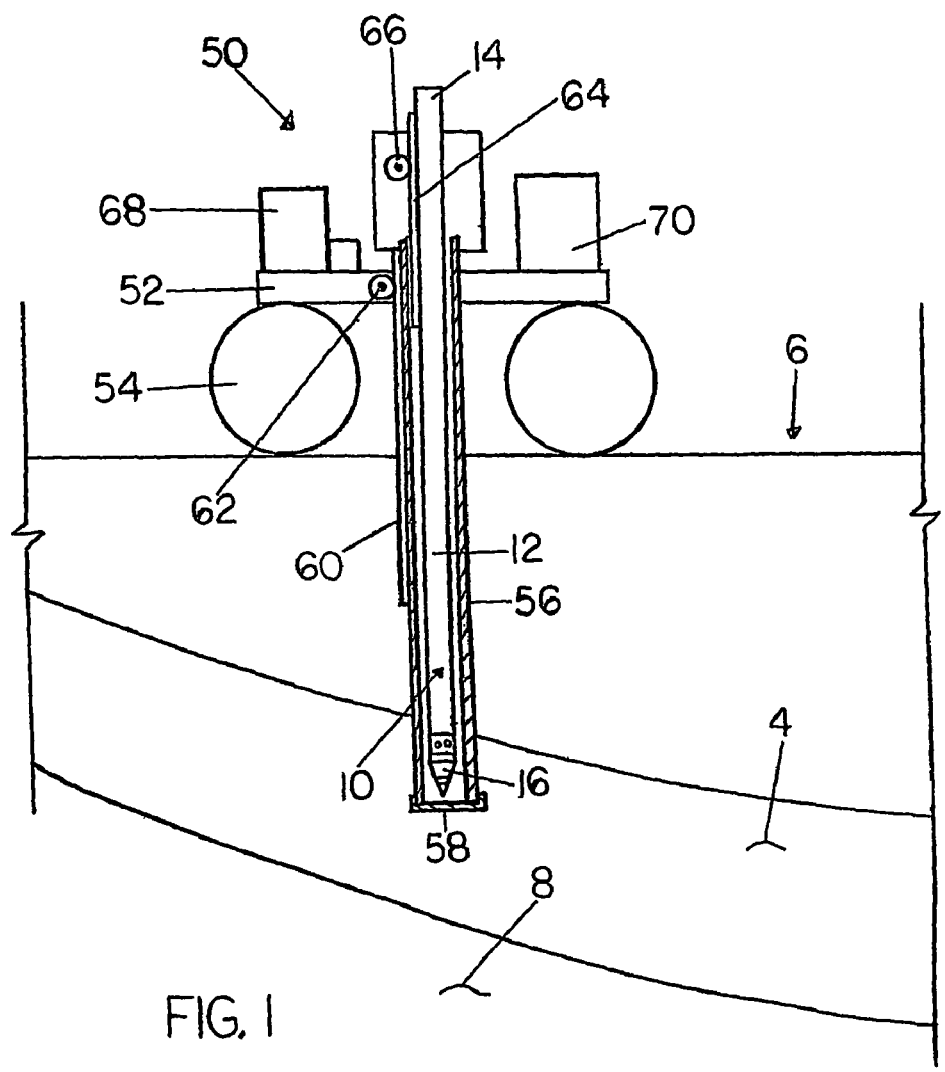
FIG. 1 is an elevational view of the probe in use at a retention pond.
Figure 2:
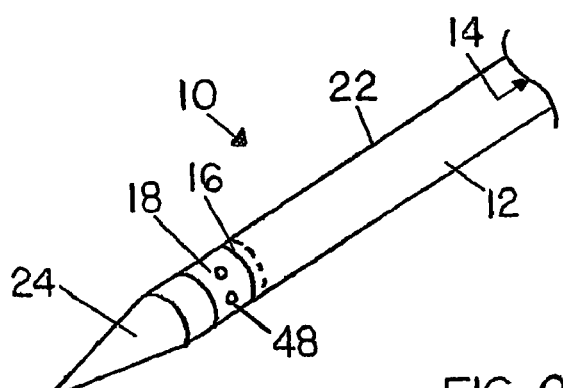
FIG. 2 is an isometric view of the probe.
Figure 3:
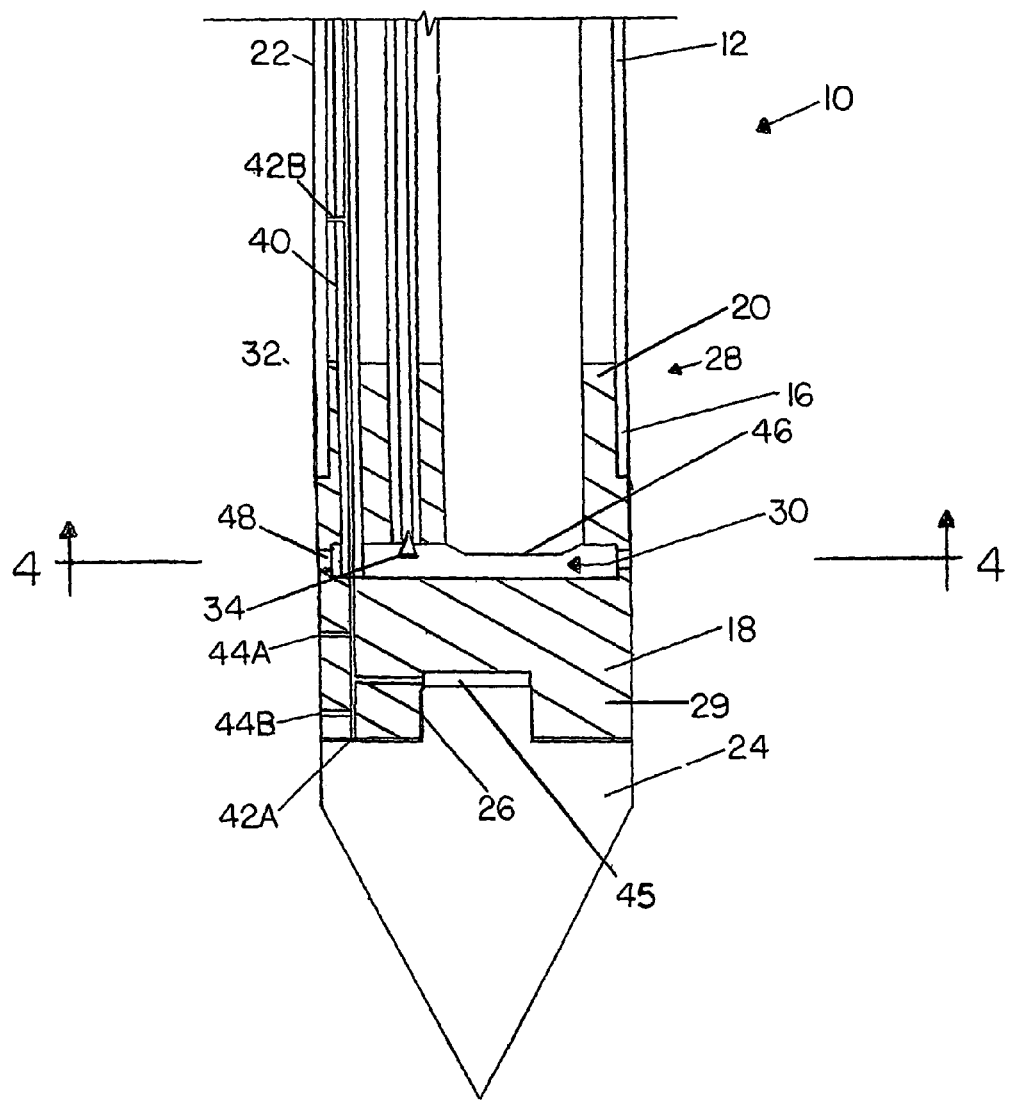
FIG. 3 is a longitudinal sectional view of the probe.
Figure 5:
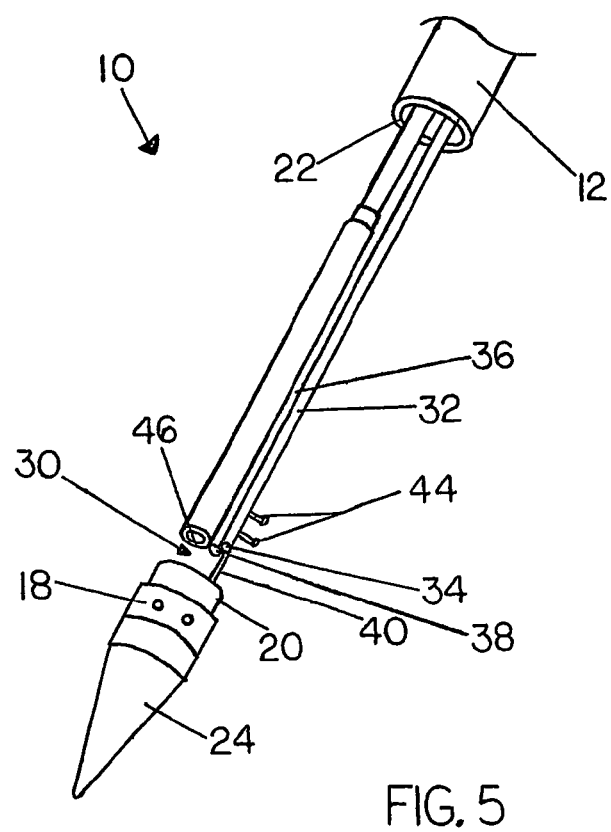
FIG. 5 is an exploded isometric view of the probe.
Figure 4:
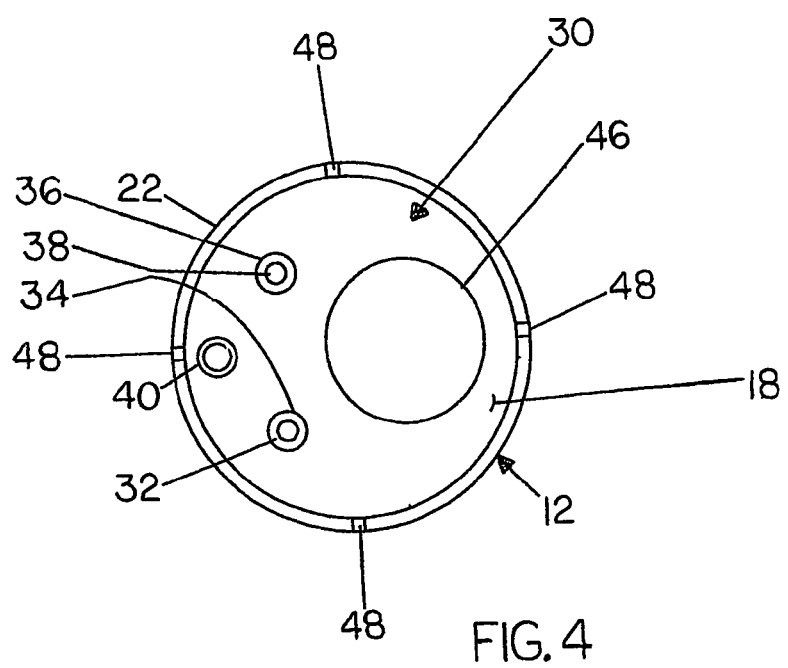
FIG. 4 is a cross sectional view along the line 4—4 of FIG. 3.

Referring to the accompanying drawings, there is illustrated a hydraulic conductivity probe generally indicated by reference numeral 10. The hydraulic conductivity probe is intended for use in measuring the hydraulic conductivity of soil in situ. The probe is particularly useful for measuring hydraulic conductivity of soil linings 4 of retention ponds 6, including municipal lagoons and manure storages and the like, of the type which do not include a geo-membrane, but rather rely generally on clay content of the surrounding soil to resist seepage into the surrounding environment 8.

The probe 10 generally includes a housing 12 in the form of an elongate rigid tubular member formed of conductive material. The housing extends in a longitudinal direction between an exposed end 14 and a soil penetrating end 16.

An insulator 18 is mounted on the soil penetrating end 16 of the housing. The insulator 18 is a cylindrical member formed of rigid insulating plastic material. The insulator includes a stepped portion 20 at an inner end thereof having a reduced diameter for snugly fitting within the interior of the tubular housing 12 at the soil penetrating end 16 thereof. An exterior diameter of the insulator 18 is arranged to mount flush with the walls 22 of the housing.

A pointed end cap 24 is provided at the soil-penetrating end of the housing for being supported on the insulator 18 so as to be electrically isolated with respect to the walls 22 of the housing. The end cap 24 is generally conical in shape, being formed of rigid conductive material and tapering towards an apex for penetration into the soil. A projection at the inner end of the end cap 24 mates with a corresponding recess 26 in the insulator 18 for securement of the end cap to the insulator. An outer diameter of the end cap at a base thereof mounts flush with the insulator 18 and the walls 22 of the housing.

The insulator is divided into an upper portion 28 and a lower portion 29. The upper portion 28 of the insulator 18 includes the stepped portion 20 noted above, so as to be supported within the tubular housing to span the interior of the tubular housing in sealing engagement with the walls 22 thereof. Hydraulic barriers such as O-rings are used between the walls 22 of the housing and the stepped portion 20 of the insulator received therein.

The upper and lower portions 28 and 29 of the insulator 18 have the same exterior diameter and are screwed together in an end to end configuration. An internal cavity 30 is defined at the intersection of the upper and lower portions when coupled together. The internal cavity 30 is located intermediately in the insulator 18 at spaced positions from both the walls 22 of the tubular housing and the end cap 24.

A water port 32 is provided in the form of a tube that communicates through the upper portion of the insulator 18, in sealed engagement therewith, from the exposed end of the housing to the internal cavity 30. The water port 32 permits water to be added to the soil at the internal cavity 30 adjacent the soil penetrating end of the housing for use in instances when the ground is not sufficiently saturated with water. A valve 34 selectively communicates with the water port 32 at a point of communication with the internal cavity 30 which is operable to selectively seal the water port closed to prevent communication of the water port with the internal cavity when the valve 34 is in its closed position.

Similarly an air port 36 is provided in the form of a tube for communication through the upper portion of the insulator 18 between the internal cavity 30 and the exposed end of the housing. The air port 36 includes a valve 38 for selectively sealing the port closed as desired. The valves 38 and 34 may be operated by conventional means including solenoid actuation for example. The air port 36 is useful for drawing air out of the internal cavity 30 before measurement of hydraulic conductivity to ensure that the surrounding soil is saturated with water.

A wiring conduit 40 is provided for communication from the exposed end of the housing through the insulator 18, in sealed engagement therewith, to electrical components of the probe. The wiring conduit 40 comprises a sealed tube, which couples an electrical power source of the probe between a first current electrode 42A and a second current electrode 42B of the probe. The second electrode 42B is coupled to the walls 22 of the housing so that the conductive material of the housing acts as a current electrode. The first electrode 42A is coupled to the end cap 24 which is also formed of conductive materials so that the end cap acts as the other current electrode. The current electrodes of the probe which act as cathode and anode respectively, are spaced apart in a longitudinal direction of the housing by the insulator 18 so as to maximise spacing between the two. When the probe is supported in an upright orientation, the anode and cathode are vertically spaced apart. Another variation for the upright orientation is the horizontal placement of the electrodes to test for anisotropy of the soil.

The wiring conduit 40 further communicates wiring therethrough for communication with electrical potential sensors 44A and 44B at longitudinally spaced locations within the insulator 18 between the anode and cathode of the probe. The electrical potential sensors 44A and 44B are spaced apart from one another at a prescribed spacing in the longitudinal direction of the housing between the side walls 22 and the end cap 24 of the housing. The electrical potential sensors serve to determine the electrical potential at two locations at a prescribed spacing within an electrical potential gradient generated by the first and second current electrodes, also referred to as the anode and cathode, when the power source is activated. This electrical potential difference can be used to calculate the electrical conductivity of the soil and pore fluid adjacent to the insulating material 18. The electrical conductivity information is used indirectly to assess the saturation status of the soil adjacent to the insulating material 18.

The conduit 40 also receives wiring which couples to a load sensor 45, in the form of a load cell located within the recess 26 of the insulator which mounts the cap 24 thereon in a manner so as to record pressure applied to the free end of the cap 24 in the longitudinal direction of the probe as the probe is inserted into the ground. The load sensor is used to monitor the penetration resistance similar to a penetrometer. This will help prevent damage to the probe if it came in contact with an impenetrable barrier such as a rock for example.

A pressure transducer 46 is mounted within the upper portion of the insulator in communication with the internal cavity 30 for measuring pressure changes within the cavity 30 while being shielded within the interior walls of the housing. The insulator 18 ensures that the pressure transducer is isolated from the walls of the housing which are charged. The transducer 46 provides continuous monitoring of pressure within the cavity and permits these readings to be displayed at the exposed end of the housing by a suitable display coupled thereto.

A plurality of apertures 48 are provided at spaced circumferencial locations about an exterior wall of the insulator 18 at the intersection of the upper and lower portions thereof for communication with the internal cavity 30. The apertures may be formed integrally in either of the upper or lower portions of the insulator 18. The apertures permit surrounding water within the soil to communicate with the cavity so that pressure changes measured by the pressure transducer 46 within the cavity 30 correspond to surrounding pressures of water within the soil about the housing surrounding the cavity 30.

As illustrated in FIG. 1, an insertion mechanism 50 may be provided to assist insertion of the probe into the soil and to act as conduit for introducing material to seal the hole, created by the probe, at the end of the test. In the illustrated embodiment, the insertion mechanism 50 is supported on a floating platform 52 including pontoons 54 for floating on a retention pond 6 in which the lining 4 is to be tested. The floating platform 52 is equipped with suitable a suitable anchoring mechanism, for example one or more conventional anchors or a tie down system for anchoring the platform at a fixed location within a body of water.

The insertion mechanism includes a probe insertion tube 56 in the form of an elongate tubular member formed of rigid material which is suitably sized to receive the housing 12 of the probe 10 slidably therethrough. A rubber end cap 58 is provided which spans a soil penetrating end of the probe insertion tube to prevent accumulation of soil and water within the tube as the tube is inserted into the ground. A rack 60 is provided alongside the tube for meshing with a pinion gear 62 driven by a respective motor to selectively drive the tube down into the ground and back up again by reversing the motor. The housing of the probe 10 may similarly include a rack 64 alongside thereof for meshing with a pinion gear 66 driven by a respective motor to selectively drive the probe relative to the tube, down through-the tube 56 to pierce the end cap 58 once the tube is in position within the lining of the pond.

A suitable control mechanism 68 permits the probe to be operated remotely from a location separate from the platform to insert and retrieve the probe, as well as subsequently seal the hole in the lining left by the probe. The control mechanism is coupled to all of the electrical components of the probe for storing data measured by the probe for later retrieval. The load sensor 45 communicates through the control mechanism 68 with the insertion mechanism in order to selectively disable the insertion mechanism in the event that excessive pressure is recorded by the load sensor due to a rock or other debris for example being impacted in the path of insertion of the probe. The load sensor 45 will give data similar to a penetrometer. This information will also be used to calculate the depth of insertion beneath the compacted clay layer as well as provide information about soil layer densities.

The control mechanism includes a data display which gives a direct read-out of the hydraulic conductivity both in metric and imperial units. The display also has the capability to store data for down-load at a later time. In addition to electrical conductivity readings, the display will show penetration resistance readings as well. An audible and/or visible signal, for example beeps and/or flashing lights, are provided on the display during the data acquisition process to indicate that the probe is functioning properly.

A sealing mechanism 70 is also supported on the platform, which is suitably arranged to dispense bentonite pellets down through the tube 56 upon removal of the probe 10 for sealing of the hole left by the probe. A tamping rod similar to the shape of the probe 10 is used to push the bentonite into the resulting cavity left by the probe after it has been completely retracted from the hole. The tamping rod will be located parallel to the probe 10 and will be moved into the position of the test hole once the probe 10 is retracted completely.

Prior to measurement of hydraulic conductivity, experiments may be performed with the probe in different known soil types having known hydraulic conductivity to permit calibration of the probe and to determine constants of the relationship between hydraulic conductivity and a measured duration of time for pressure at the cavity to vary between first and second pressure conditions, previously induced by electro-osmotic flow, under a hydraulic potential pressure gradient.

Also prior to measurement of hydraulic conductivity it may be useful to determine the electrical conductivity of the soil at the site of measurement, as an indication of the moisture content of the soil. This is accomplished by first inserting the probe into the soil as noted above at which point the electrical potential gradient between the cathode and anode is established. While the electrical potential gradient is being applied, electrical potential difference at the sensors 44 is measured at spaced positions within the gradient. Electrical conductivity can then be calculated using the two known electrical potentials and the known prescribed spacing of the points of measurement in a known generated electrical potential gradient. If results of the measured electrical conductivity indicate that the soil is too dry, water may be added through the water port 32 to the soil surrounding the cavity 30 by appropriately controlling the valve 34 of the water port.

The compacted clay liners remain saturated beneath lagoons and manure storages, however, in other applications it may be desirable to add water regardless of electrical conductivity measurements in order to ensure that the surrounding soil is properly saturated with water. Before measurement of hydraulic conductivity it is also important that any air within the cavity 30 and surrounding soil be removed by opening the corresponding valve of the air port 36 or manually fill the cavity prior to insertion of the probe 10. The valves connecting both the air and water ports to the cavity must be sealed closed before proceeding with any measurements. It is also desirable to wait for pressure as measured by the transducer 46 to stabilise at a constant value when water has been added before proceeding with the measurement of hydraulic conductivity.

Measurement of hydraulic conductivity begins by first measuring pressure as determined by the pressure transducer 46 within the cavity and recording this pressure as a first pressure condition. The electrical potential gradient is then applied by the power source coupled between the cathode and anode until a prescribed pressure as measured by the transducer 46 is reached. The prescribed pressure is preferably a set point pressure, which is adjustable in order to prevent the electrical gradient from being applied too long. If the prescribed pressure takes too long to achieve, a duration threshold may be preferable for discontinuing the applied electrical potential gradient before soil properties are affected. Alternatively a prescribed duration for application of the electrical potential gradient may be desirable.

Once the electrical potential gradient has been removed, pressure is again measured within the cavity 30 by the transducer 46 and recorded as a second pressure condition. The measured duration is then recorded for pressure of water within the cavity to return from the second pressure condition to the first pressure condition under hydraulic potential gradient. The hydraulic conductivity may then be calculated using the prescribed relationship between hydraulic conductivity and the measured duration.

The probe readings should be restricted to one or two electrical pulse applications at any given location.

In further applications, the electro-osmotic conductivity may also be determined by recording the duration for which the electrical potential gradient is applied in addition to measuring the respective first and second pressure conditions at the start and finish of the recorded duration of the application of the electrical potential gradient.

In operation, the gradient causes a net flow of water in the surrounding soil from the cathode at the end cap 24 to the anode at the walls 22 of the housing so that there is produced a net flow of water into the cavity 30 in the housing. When the electrical potential gradient is removed, the decrease in pressure of water in the cavity as produced by the net out-flow due to pressure dissipation is recorded by the transducer and is used for establishing the hydraulic conductivity of the soil. The probe is ideally used in soils having a clay content of at least five percent.

As noted above, the probe can be used to measure the hydraulic conductivity of the clayey soil beneath manure storages, municipal lagoons and other retention ponds that do not have geo-membrane liners. Hydraulic conductivity of the soil can be used to estimate the seepage through it. There are no in situ methods currently available for measuring the hydraulic conductivity of soils beneath manure storages and lagoons. The law requiring minimal seepage therefore, cannot be reliably enforced once the manure storage has been in operation. The probe will also be of interest to soil scientists, engineers who are dealing with soil physical properties. The probe can be used as a tool for periodically monitoring the integrity of the clay liner beneath earthen manure storages, municipal lagoons, retention ponds for industrial waste etc. It can also be used, for measuring the hydraulic conductivity of saturated soils in situ.

The probe operates because clay particles in the soils are negatively charged and usually attract positively charged ions in the pore fluid. When a DC electrical potential gradient is applied to the soil, the positively charged ions will move towards the cathode 24, which comprises the negative electrode, and the negatively charged ions will move towards the anode 22, which comprises the positive electrode. However, the positive ions, being larger, tend to drag more water molecules along with them compared to the negative ions. As a result there is a net flow of water towards the cathode. This net flow is called electro-osmotic flow. The probe uses this principle to initiate a small quantity of net flow towards the cavity containing the pressure transducer, which monitors the fluid pressure in the probe cavity. When the DC electrical potential gradient is removed, the inequality in fluid pressure created in the vicinity of the probe will tend to equalize by fluid flow in the reverse direction under hydraulic gradients. As the fluid flows in the reverse direction under hydraulic gradients, the pressure transducer will measure a decline in pressure within the cavity. The rate of decline of the pressure of fluid in the cavity is directly proportional to the hydraulic conductivity of the soil surrounding the probe. A probe constant can be established by calibrating in soils with known saturated, hydraulic conductivity. The time rate of change of pressure and the probe constant information is used by a module within the meter to calculate and display the hydraulic conductivity of the soil surrounding the probe. Since the water volumes are small the measurement time is fast. The application of electro-kinetic principles to move the water towards the pressure sensing area of the probe is unique in this method. The concept behind the electronic conversion of the response from the sensor to intelligible hydraulic conductivity readings is unique.

Again as noted above, additional features include potential electrodes 44A and 44B which can be used to measure the electrical conductivity of the soil using the four-point electrode method. This information is useful for getting a feel for the ionic concentration in the pore water. It can also indirectly indicate whether the soil surrounding the tip is dry or wet. If the soil is dry, then water could be introduced through the tubes prior to measurement. One tube is used to introduce the water into the probe cavity and the other tube is used to bleed trapped air in the cavity. The air bleed is necessary for the optimum performance of the pressure transducer.

Hydraulic conductivity refers to the ability of soil to allow water movement. In sewage lagoons, for example, it is important to determine hydraulic conductivity of the lagoon lining in order to determine the degree of seepage from the lagoon. Current methods of measuring hydraulic conductivity require the removal of a core sample from the clay underneath the lagoon, which is then transported back to the laboratory for the testing. There is currently no feasible method for measuring hydraulic conductivity of lagoon lining, making it impossible to enforce government regulations regarding seepage of sewage into the groundwater.

The method disclosed herein can quickly determine the hydraulic conductivity of soil. This method and the probe 10 are particularly useful in applications such as sewage lagoons, in which a core sample is difficult to obtain. The method involves using the electro-osmotic conductivity of clay to draw up minute amounts of water into a pressure sensing device, and then removing the electrical stimulus, allowing the water to recede. The rate at which the water flows back into the soil (monitored by pressure transducers) is proportional to the hydraulic conductivity of the soil.

The probe 10 applies the above principle, in the form of a telescopic probe, approximately 2 inches or less in diameter, with a cone-shaped tip (3 inches in length) for penetration into the ground. As described above, a large watertight insertion tube 56 with a rubber end is first lowered through the water or sewage to the clay bed. The probe is then passed through the tube and punctures the rubber end, passing into the ground. An electrical potential gradient is then applied to the tip of the probe, drawing up approximately 5–500 µL water. This amount of water is minute enough to allow fast measurement of the hydraulic conductivity, while not disturbing the soil composition. The electrical gradient is then removed, and the pressure dissipates when water moves back into the clay. This measurement is much faster than the current method of laboratory testing; as such a small quantity of water is used, allowing the water to dissipate more quickly. A pressure transducer is located within the probe and the change in pressure of the water over time can be used to calculate the hydraulic conductivity of the clay. In this manner, sewage lagoons may be monitored on site for the ability of sewage to seep from the lagoon.

Anywhere the hydraulic conductivity of soils information is needed, this probe can be used. For example, it can be used in the petroleum industry to assess the hydraulic conductivity of the formation. Oil movement in formations can be predicted by measuring the water movement through oil-bearing formations. At present, the oil industry measures this parameter in the laboratory using cores drilled from the formations. The in situ method might be more advantageous because it is fast and a lot less expensive.

While one embodiment of the present invention has been described in the foregoing, it is to be understood that other embodiments are possible within the scope of the invention. The invention is to be considered limited solely by the scope of the appended claims.

REFERENCES

1. American Society for Testing and Materials (ASTM). D 5084–90. Standard test method for measurement of hydraulic conductivity of saturated porous materials using a flexible wall permeameter. Annual Book of ASTM Standards.
2. Daniel, E. David. 1989. In situ hydraulic conductivity tests for compacted clay. Journal of Geotechnical Engineering, Vol. 115, No. 9 Pg. 1205–1226 ÓASCE.
3. Demir, Z. and Narasimhan, T. N. 1994. Improved interpretation of Hvorslev tests. Journal of Hydraulic Engineering, Vol. 120, No. 4. Pg. 477–494
4. Domenico, P. A. and Schwartz, F. W. 1997. *Physical and Chemical Hydrogeology*, second edition. John Wiley & Sons, Inc.
5. Fetter, C. W. 1994. *Applied Hydrogeology*, Third edition. Prentace Hall.
6. Hvorlsev, M. J. 1951. Time Lag and Soil Permeability in Ground Water Observations. Corps of Engineers, U.S. Army. Bulletin no.36. Waterways Experiment Station.
7. Wanielista, M., Kersten, R. and Eaglin, R. 1997. *Hydrology—Water Quantity and Quality Control*, Second edition. John Wiley & Sons, Inc.
8. Yeung, A. T., Gopinath, Sreekumar, Menon, Rajendra, M., Scott, T. B., Datla, Subbaraju. 1993. Electro-kinetic extraction of contaminants form polluted soil. Waste Management Proceedings of the Gulf Coast Hazardous Substance Reasearch Center's 1993 Symposium on Emerging Technologies: Metals, Oxydation, and Separation. Vol. 13, No.5–7. Pg 539–540.

All documents and publications referred to or mentioned in the foregoing are incorporated herein by reference.

The invention claimed is:

1. A method of measuring hydraulic conductivity in soil, said method comprising:

providing a probe having an electrical potential gradient device for generating an electrical potential gradient and a pressure sensing device for measuring changes in pressure;

inserting the probe into the soil;

measuring a first pressure condition within the soil using the pressure sensing device of the probe;

inducing an electro-osmotic flow in the soil and causing a fluid pressure gradient by applying an electrical potential gradient to the soil using the electrical potential gradient device of the probe for an elapsed period of time;

measuring a second pressure condition within the soil using the pressure sensing device of the probe;

removing the application of the electrical potential gradient to the soil using the electrical potential gradient device of the probe after the elapsed period of time has expired;

measuring a duration for condition of the soil to return from the second pressure condition to a pressure approaching the first pressure condition; and calculating hydraulic conductivity based upon a prescribed relationship of hydraulic conductivity and the measured duration.

2. The method according to claim 1 including calibrating the probe to determine the prescribed relationship between hydraulic conductivity and the measured duration prior to calculating the hydraulic conductivity.

3. The method according to claim 1 including applying the electrical potential gradient until a pressure condition of the soil reaches a prescribed pressure.

4. The method according to claim 3 wherein the prescribed pressure is an adjustable set point pressure.

5. The method according to claim 1 including applying the electrical potential gradient for a prescribed duration.

6. The method according to claim 1 including wetting the soil before inducing the electro-osmotic flow and before measuring the first and second pressure conditions.

7. The method according to claim 6 wherein the probe includes a water port for introducing water into the soil, the method including sealing the water port before measuring the first and second pressure conditions.

8. The method according to claim 6 including waiting for a pressure condition of the soil to become near equilibrium condition after wetting the soil before measuring the first and second pressure conditions.

9. The method according to claim 1 including bleeding air surrounding the pressure sensing device within the soil before measuring the first and second pressure conditions.

10. The method according to claim 9 wherein the probe includes an air port for removing air from the soil surrounding the pressure sensing device, the method including sealing the air port before measuring the first and second pressure conditions.

11. The method according to claim 1 wherein the probe includes two electrical potential sensors at prescribed spaced locations within the electrical gradient generated by the electrical potential gradient device, the method including measuring electrical potential at each of the sensors and calculating electrical conductivity.

12. The method according to claim 11 including wetting the soil before measuring the first and second pressure conditions if the calculated electrical conductivity indicates the soil is dry.

13. The method according to claim 1 including recording the elapsed period of time of the electrical potential gradient and calculating electro-osmotic conductivity based upon the elapsed period of time and a difference between the first and second pressure conditions.

14. The method according to claim 1 including inserting the probe into soil in situ.

15. The method according to claim 1 including inserting the probe into clay soil beneath a retention pond.

16. A method of measuring hydraulic conductivity in soil, said method comprising:

providing a probe having an electrical potential gradient device for generating an electrical potential gradient and a pressure sensing device for measuring changes in pressure;

providing a probe insertion tube for slidably receiving the probe therethrough;

inserting the probe insertion tube into the soil prior to insertion of the probe;

inserting the probe into the soil by inserting the probe through the probe insertion tool;

measuring a first pressure condition within the soil using the pressure sensing device of the probe;

applying an electrical potential gradient to the soil using the electrical potential gradient device of the probe for an elapsed period of time;

measuring a second pressure condition within the soil using the pressure sensing device of the probe;

removing the application of the electrical potential gradient to the soil using the electrical potential gradient device of the probe after the elapsed period of time has expired;

measuring a duration for condition of the soil to return from the second pressure condition to a pressure approaching the first pressure condition;

calculating hydraulic conductivity based upon a prescribed relationship of hydraulic conductivity and the measured duration.

removing the probe from the probe insertion tube subsequent to measurement of the first and second pressure conditions;

introducing soil sealing material through the probe insertion tube to fill a cavity in the soil formed by the probe; and removing the probe insertion tube from the soil.

17. The method according to claim 16 wherein the soil sealing material comprises bentonite pellets.

18. A probe for measuring hydraulic conductivity in soils, the probe comprising:

a housing being suitably shaped for insertion into the ground, the housing including side walls extending in a longitudinal direction between an exposed end of the housing and a pointed end cap at a soil penetrating end of the housing, the pointed end cap being insulated with respect to the side walls of the housing;

an electrical potential gradient device for generating an electrical potential gradient in the ground surrounding the housing, the electrical potential gradient device comprising:

a first electrode coupled to the pointed end cap at the soil penetrating end of the housing and a second electrode coupled to side walls of the housing in which the first and second electrodes are insulated from one another at spaced locations from one another in the longitudinal direction of the housing; and an electrical power supply coupled between the first and second electrodes; and a pressure sensing device for measuring changes in pressure in porewater within the ground.

19. The probe according to claim 18 wherein the housing comprises an elongate tubular member.

20. The probe according to claim 18 wherein the electrical potential gradient device and the pressure sensing device are located adjacent the soil penetrating end of the housing.

21. The probe according to claim 20 wherein there is provided an elongate probe insertion tube for receiving the housing therein, a soil penetrating end of the insertion tube being formed of resilient material permitting the pointed end of the housing to be penetrated therethrough.

22. The probe according to claim 18 wherein there is provided two electrical potential sensors supported on the housing at prescribed spaced locations within the electrical gradient generated by the electrical potential gradient device.

23. The probe according to claim 18 wherein there is provided a plurality of apertures in the housing for communication with an internal cavity of the housing supporting the pressure sensing device therein.

24. The probe according to claim 23 wherein the pressure sensing device comprises a pressure transducer.

25. The probe according to claim 23 wherein there is provided an air port communicating between the exposed end of the housing and the internal cavity of the housing.

26. The probe according to claim 25 wherein the air port includes a valve for selectively sealing the air port in a closed position.

27. The probe according to claim 25 wherein there is provided a water port communicating between the exposed end of the housing and the internal cavity of the housing.

28. The probe according to claim 27 wherein the water port includes a valve for selectively sealing the water port in a closed position.

* * * * *